United States Patent
Solf et al.

(10) Patent No.: US 7,750,305 B2
(45) Date of Patent: Jul. 6, 2010

(54) INTEGRATED MULTI-CHANNEL TIME-TO-DIGITAL CONVERTER FOR TIME-OF-FLIGHT PET

(75) Inventors: Torsten J. Solf, Aachen (DE); Peter Fischer, Ketsch (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 87 days.

(21) Appl. No.: 12/304,135

(22) PCT Filed: May 29, 2007

(86) PCT No.: PCT/US2007/069835

§ 371 (c)(1),
(2), (4) Date: Dec. 10, 2008

(87) PCT Pub. No.: WO2007/146587

PCT Pub. Date: Dec. 21, 2007

(65) Prior Publication Data

US 2009/0250616 A1    Oct. 8, 2009

Related U.S. Application Data

(60) Provisional application No. 60/804,864, filed on Jun. 15, 2006.

(51) Int. Cl.
*G01T 1/166* (2006.01)
*H03L 7/08* (2006.01)
(52) U.S. Cl. .................. 250/363.04; 327/158; 327/159
(58) Field of Classification Search ............ 250/363.01, 250/363.02, 363.04, 363.07; 327/158, 159; 331/1 A
See application file for complete search history.

(56) References Cited

U.S. PATENT DOCUMENTS

| 6,501,706 | B1 | 12/2002 | West | |
|---|---|---|---|---|
| 2003/0076181 | A1* | 4/2003 | Tabatabaei et al. | 331/57 |
| 2005/0122846 | A1 | 6/2005 | Bolli et al. | |
| 2008/0069292 | A1* | 3/2008 | Straayer et al. | 377/46 |

OTHER PUBLICATIONS

Weinlader et al, "An Eight Channel 36GSample/s CMOS Timing Analyzer," IEEE International Solid-State Circuits Conference, 2000.

(Continued)

*Primary Examiner*—David P Porta
*Assistant Examiner*—Mark R Gaworecki

(57) ABSTRACT

In a radiation detector (10) for a time of flight positron emission tomography (PET) scanner (2), a radiation sensitive member (20) generates a signal (22) indicative of a radiation detection event. A time to digital converter (34) includes digital delay elements (40) operatively interconnected as a ring oscillator (36, 36') and readout circuitry (50, 52, 60, 82, 84, 86, 88) configured to generate a timestamp for the radiation detection event based at least on a state of the ring oscillator when the signal is generated. Delay trim elements (46) operatively connected to the digital delay elements set a substantially common delay for the digital delay elements. Additionally or alternatively, the digital delay elements (40) include readout buffers (48') having transition times substantially longer than a delay of the digital delay elements, analog to digital converters (82, 84) digitize values of the delay elements, and decoding circuitry (86, 88) computes the state of the ring oscillator (36') based on the digitized values.

22 Claims, 7 Drawing Sheets

OTHER PUBLICATIONS

Mota et al., "A four channel, self-calibrating, high resolution, Time to Digital Converter," IEEE Int'l Conf. on Electronics, Circuits, and Systems, CERN, Geneva, Switzerland, 1998.

Christiansen, "An Integrated CMOS 0.15 ns Digital Timing Generator for TDC's and . . . ," IEEE Transactions on Nuclear Science, CERN, Geneva, Switzerland, Aug. 1995.

Abas et al., "Design of Sub-10-Picoseconds On-Chip Time Measurement Circuit," Design Automation and Test in Europe Conference and Exhibition, Feb. 2002.

Boujrad et al., "A digital TDC with a reduced number of delay line cells," Nuclear Instruments and Methods in Physics Research A 486, pp. 803-812, 2002.

Ljuslin et al., "An Integrated 16-channel CMOS Time to Digital Converter.", IEEE Transactions on Nuclear Science, 41, pp. 1104-1108, (1994).

Chen et al., "A Precise Cyclic CMOS Time-to-Digital Converter with Low Thermal Sensitivity," IEEE Nuclear Science Symposium Conference Record, Rome, Italy, Oct. 2004.

Jansson et al., "A delay Line Based CMOS Time Digitizer IC with 13 ps Single-shot Precision," IEEE International Symposium on circuits and Systems, Kobe, Japan, May 2005.

Mota et al., "A flexible multi-channel high-resolution Time-to-Digital Converter ASIC," IEEE Nuclear Science Symposium, Lyon, France, Oct. 2000.

Kalisz, J.; Review of methods for time interval measurements with picosecond resolution; 2004; Institute of Physics Publishing; Metrologia; 41:17-32.

Back, T., et al.; An educational tool for demonstrating the TOF-PET technique; 2001; Nuclear Instruments and Methods in Physics Research; A 471:200-204.

Nissinen, L., et al.; A CMOS Time-to-Digital Converter based on a Ring Oscillator for a Laser Radar; 2003; European Solid-State Circuits IEEE; pp. 469-472.

* cited by examiner

INTEGRATED MULTI-CHANNEL TIME-TO-DIGITAL CONVERTER FOR TIME-OF-FLIGHT PET

CROSS REFERENCE TO RELATED APPLICATIONS

This application claims the benefit of U.S. provisional application Ser. No. 60/804,864 filed Jun. 15, 2006, which is incorporated herein by reference.

The present application relates to the data sampling, timestamping, and related arts. It finds particular application in time-to-digital converters for providing sub-nanosecond-resolution timestamping of radiation detection events in time-of-flight positron emission tomography (PET) scanning, and is described with particular reference thereto. However, the following finds more general application in time-to-digital conversion in other medical applications, generally, and in applications, methods, and devices employing such time-to-digital conversion, such as timing of light or light-speed events, timing of radiation detection events in nuclear processes, timing of other time-sensitive events, and so forth.

In PET, a radiopharmaceutical is administered to a human patient or other imaging subject. The radiopharmaceutical produces radiation decay events that emit positrons, which travel a very short distance before rapidly interacting with a nearby electron of the surrounding imaging subject in an electron-positron annihilation event that produces two oppositely directed gamma rays. The gamma rays are detected by radiation detectors surrounding the imaging subject as two substantially simultaneous radiation detection events that define a line of response (LOR) therebetween.

Although the gamma rays are detected "substantially simultaneously", if one of the two involved radiation detectors is closer to the electron positron annihilation event than the other radiation detector, then there will be a small time difference between the two radiation detection events. Since gamma rays travel at the speed of light and the detectors are only about two meters or less apart, this time difference between detections is typically around a nanosecond or less, and may be as low as zero if the positron-electron annihilation event is equidistant from the two detectors along the paths of the gamma rays. In time-of-flight PET (TOF-PET), the radiation detectors operate at sufficiently high speed to enable measurement of small time-of-flight differences, which are used to localize the electron positron annihilation events along the LORs. A datum combining the LOR with time-limiting information from the time-of-flight measurement component is sometimes called a histoprojection.

For TOF-PET, radiation detection events should be timestamped with sub-nanosecond temporal resolution. Generally, as temporal resolution improves, the spatial resolution of the localization of the annihilation event along the LOR also improves. An integrated, multi-channel, high performance and low power readout architecture is called for, which performs both digitization of the radiation detection event (energy and spatial location or distribution) and digitization of the time of occurrence of the radiation detection event (time-to-digital conversion) of more than one-hundred channels with sub-nanosecond timing resolution. Discrete time-to-digital converters which are available are high-input power devices, and are not readily adapted for use in TOF-PET. Integrated solutions in which detection and processing is implemented on a single chip would be advantageous.

Existing time-to-digital converters employ ring oscillators synchronized by a central reference clock. The time-to-digital conversion is based on latching the status of the delay elements of the ring oscillator when a trigger event (such as a radiation detection event in the case of PET scanning) is detected. A ring oscillator includes a series interconnection of several digital delay elements, such as inverters or buffers. The output of the delay chain is fed back to the input. The configuration has no stable state if the delay chain includes an inverting connection.

Difficulties arise, however, in achieving sufficiently high precision when using ring oscillators for time-to-digital conversion at sub-nanosecond resolution. To achieve such high temporal resolution, the delay of each digital delay element is made short, e.g. a few picoseconds to a few tens of picoseconds. For example, in CMOS sufficiently fast devices are achieved by going to short gate lengths. With fast, short-gate-length devices, however, matching between devices is typically poor, and delay variations between different digital delay elements in the ring oscillator typically become substantial, which limits temporal precision of the timestamping. Attempting to overcome these problems by redesigning the digital delay devices, for example by going to longer gate lengths, reduces overall speed and increases capacitance and device power consumption. Jitter in the ring oscillator can also be addressed by post-acquisition processing, such as by making a digital correction to the output of the time-to-digital converter. However, such correction adds complexity and increases bandwidth and system cost. Moreover, even with such correction some jitter remains.

The present application provides new and improved time-to-digital converters, radiation detectors, PET scanners, and methods relating thereto which overcome the above-referenced problems and others.

In accordance with one aspect, time-of-flight PET scanner is disclosed. A radiation detector is disposed to detect radiation emitted from an imaging region. The radiation detector includes at least one time-to-digital converter for timestamping radiation detection events. The time-to-digital converter includes: a plurality of digital delay elements operatively interconnected as a ring oscillator; delay trim elements operatively connected to the digital delay elements and configurable to set a substantially common delay for the digital delay elements; and readout circuitry configured to generate a timestamp based at least on a state of the ring oscillator responsive to a radiation detection event.

In accordance with another aspect, a time-to-digital converter is disclosed. A plurality of digital delay elements are operatively interconnected as a ring oscillator. Delay trim elements are operatively connected to the digital delay elements and configurable to set a substantially common delay for the digital delay elements. Readout circuitry is configured to generate an output indicative of a state of the ring oscillator responsive to a trigger event.

In accordance with another aspect, a radiation detector is disclosed. A radiation-sensitive member generates a signal indicative of a radiation detection event. A time-to-digital converter includes a plurality of digital delay elements operatively interconnected as a ring oscillator, delay trim elements operatively connected to the digital delay elements and configurable to set a substantially common delay for the digital delay elements, and readout circuitry configured to generate a timestamp for the radiation detection event based at least on a state of the ring oscillator when the signal is generated.

In accordance with another aspect, a method is disclosed for calibrating a ring oscillator comprising a plurality of delay elements operatively interconnected as a ring oscillator. Histogram data are determined of outputs of the ring oscillator responsive to randomized trigger events. Delays of the delay elements are adjusted based on the histogram data to set a substantially common delay for the delay elements.

In accordance with another aspect, a time-to-digital converter is disclosed. A plurality of digital delay elements are operatively interconnected as a ring oscillator. The digital delay elements include readout buffers having transition times that are substantially longer than a delay of the digital delay elements. Analog-to-digital converters digitize values of the delay elements responsive to a trigger event. Decoding circuitry computes a state of the ring oscillator corresponding to the trigger event based on the digitized values. The computed state has a temporal resolution smaller than the delay of the digital delay elements.

In accordance with other aspects, radiation detectors and time-of-flight PET scanners are disclosed which employ the time-to-digital converter set forth in the preceding paragraph.

One advantage resides in improved temporal resolution.

Another advantage resides in periodic, or optionally real-time, correction of delay differences in the delay elements of a time-to-digital converter.

Another advantage resides in providing a time-to-digital converter with low power consumption.

Another advantage resides in providing a radiation detector with integrated high-resolution time-to-digital conversion.

Another advantage resides in providing a time-of-flight PET scanner with detectors including integrated timestamping.

Another advantage resides in simultaneous timestamping and signal integration for each channel, providing the time, energy, and position parameters for time-of-flight PET.

Still further advantages of the present invention will be apparent to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically shows a time-of-flight positron emission tomography (PET) scanner.

FIG. 2 diagrammatically shows a block diagram of the radiation detector of FIG. 1 including principal components of the time-to-digital converter.

Figure 3:
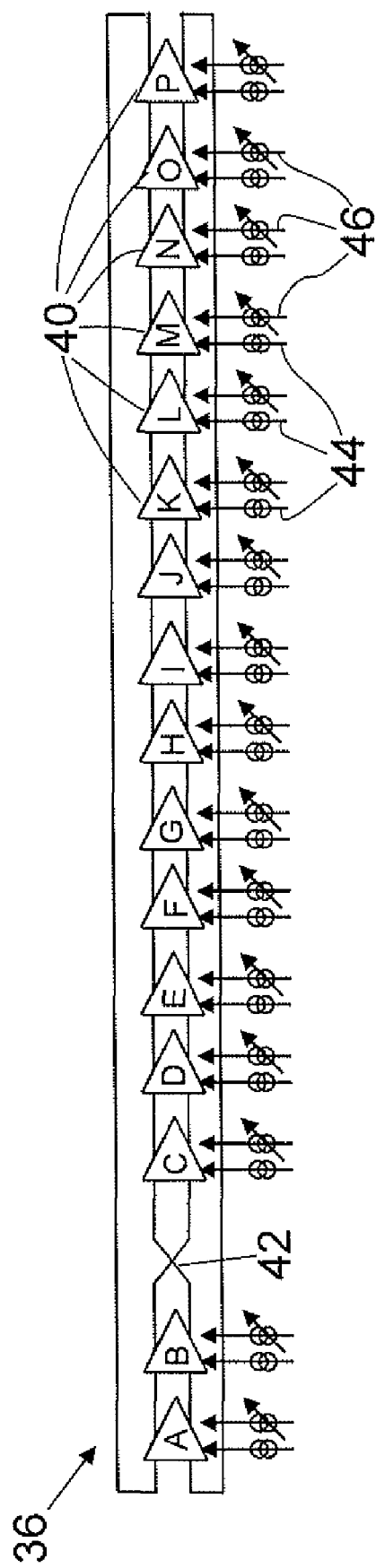
FIG. 3 shows an electrical schematic diagram of principal components of the ring oscillator of the time-to-digital converter of FIG. 2.
Figure 6:
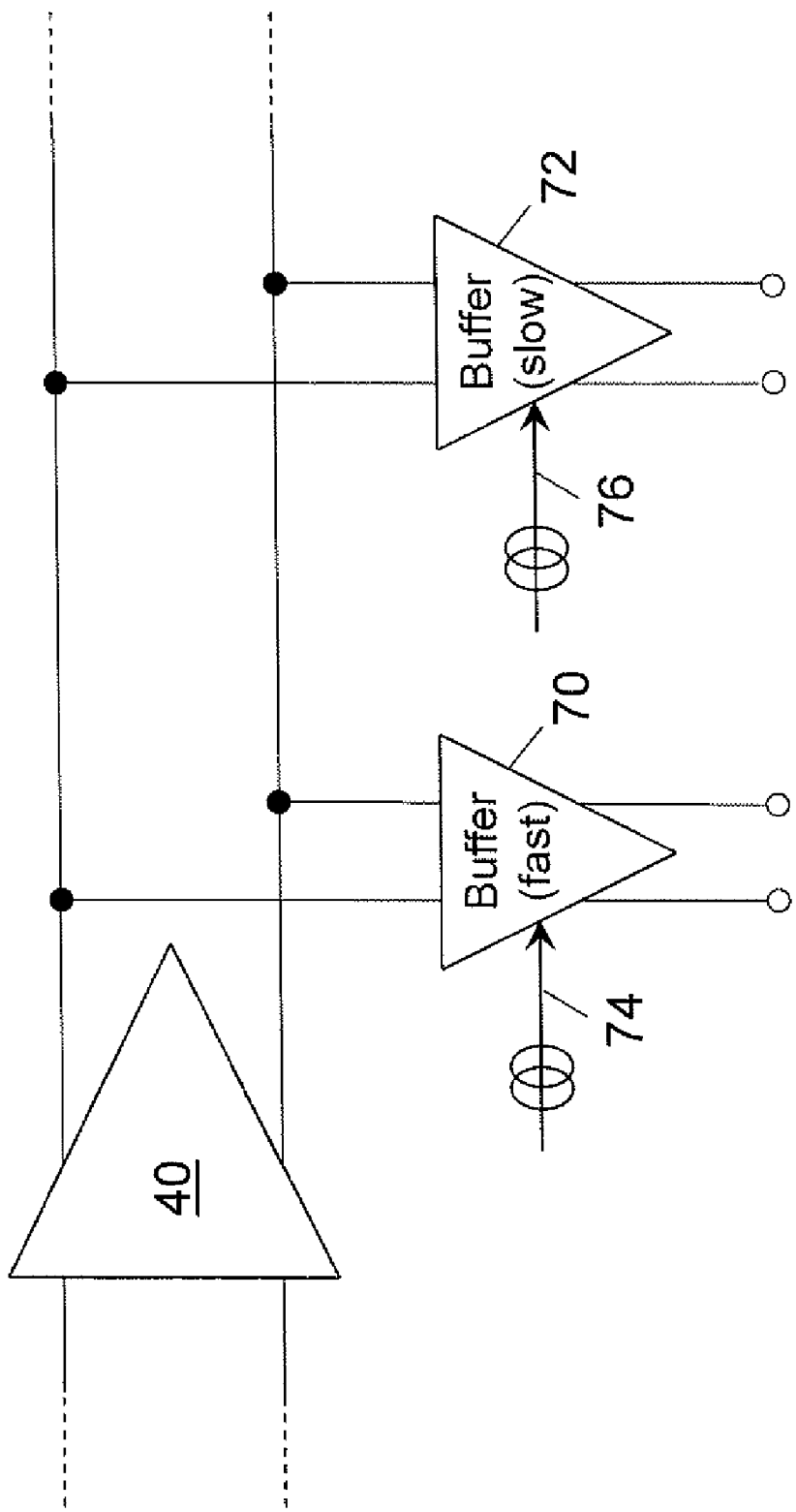

FIG. 6 diagrammatically shows an oversampling approach for increasing the temporal resolution of the ring oscillator of FIG. 3.

Figure 1:
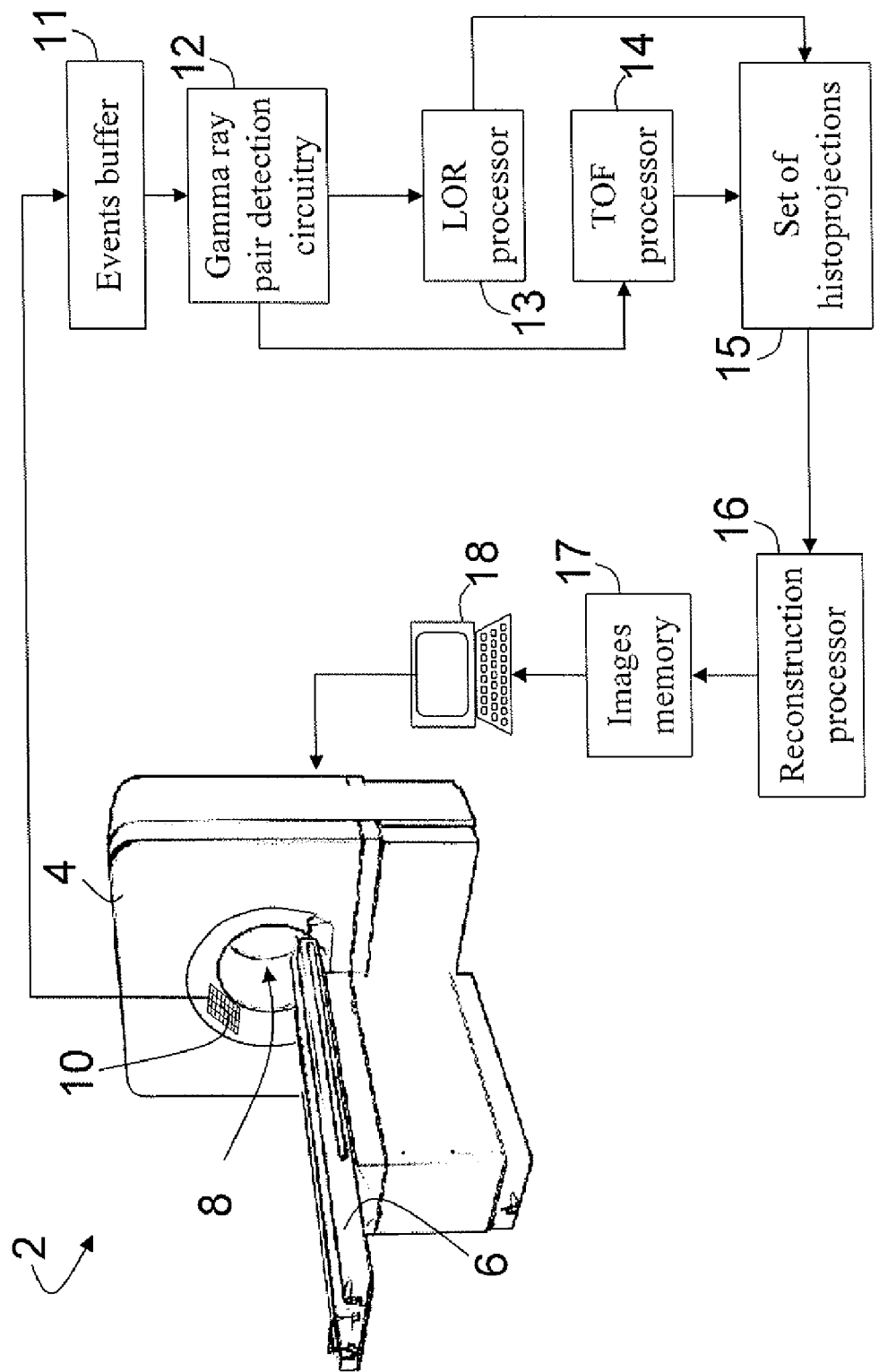
Figure 7:
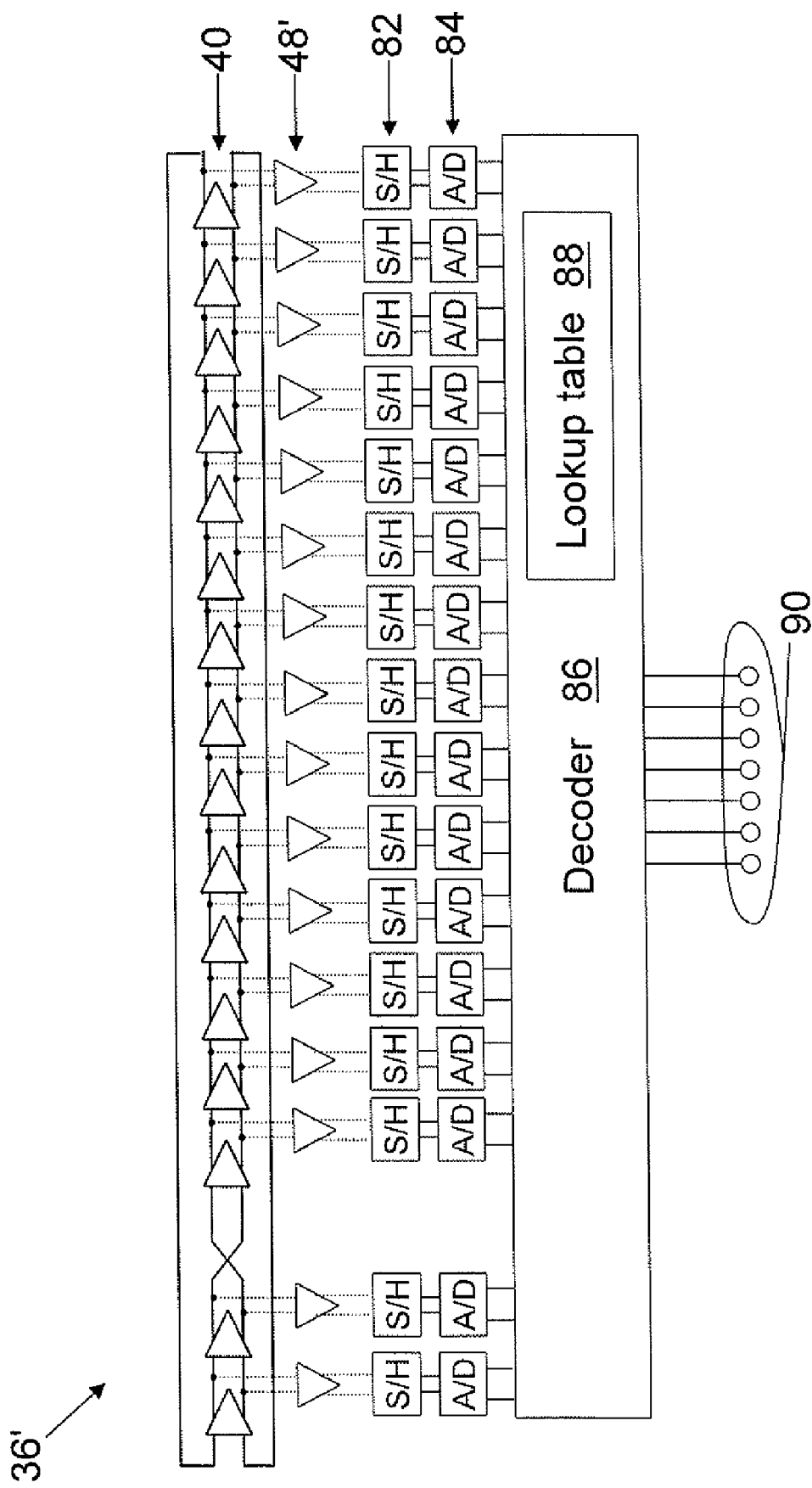

FIG. 7 diagrammatically shows an electrical schematic diagram of principal components of another ring oscillator suitably used in a time-to-digital converter of the radiation detector of FIG. 1.

Figure 8:
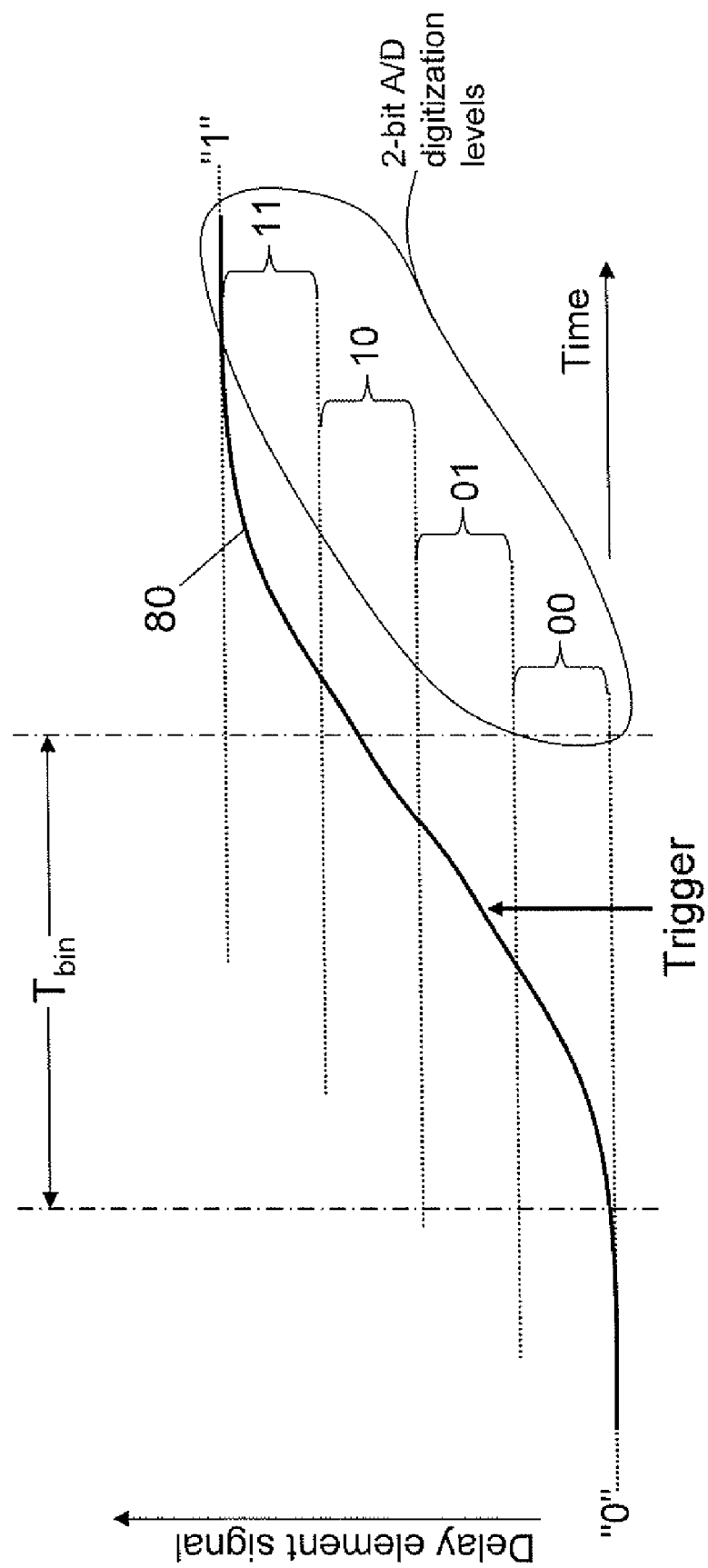

FIG. 8 diagrammatically shows an off-to-on transition of one of the digital delay elements of the ring oscillator of FIG. 7.

With reference to FIG. 1, a time-of-flight positron emission tomography (TOF-PET) scanner 2 includes a housing 4, and couch 6 or other patient support. The housing 4 defines a bore-type imaging region 8. A radiation detector array 10 arranged to view the imaging region 8. It is to be appreciated that the single shown radiation detector array 10 is illustrative—the scanner 2 typically includes one or more rings of such detector arrays encircling the imaging region 8 to acquire data at substantially any angle. Additionally, it is to be appreciated that the radiation detector array 10 is diagrammatically illustrated—typically, the radiation detectors are housed within the housing 4 of the scanner 2 and thus are typically not visible from the outside, and typically each ring of radiation detectors includes hundreds or thousands of radiation detector elements. In some PET scanners, only a single ring of radiation detectors is provided; in others, two, three, four, five, or more rings of radiation detectors are provided. Moreover, in some embodiments the radiation detectors may be arranged as one or more arrays on one or more detector heads, as in a gamma camera arrangement. The detector heads may be movable in various ways, such as movable toward or away from the patient, movable around the patient, or so forth. The couch 16 or other support positions a human patient or other imaging subject in the imaging region 8. Optionally, the couch 6 is linearly movable in the axial direction generally transverse to the rings of radiation detectors 10 to facilitate acquisition of three-dimensional imaging data. Additionally or alternatively, the imaging subject can be held stationary, and a plurality of rings of radiation detectors used to acquire three-dimensional TOF-PET imaging data. In yet other embodiments, only a single ring of detectors is provided, the imaging subject remains stationary, and the resulting image is two-dimensional.

A suitable radiopharmaceutical is administered to the patient or other imaging subject prior to initiation of TOE-PET imaging. The radiopharmaceutical includes a radioactive substance that undergoes radioactive decay events that emit positrons. The emitted positrons rapidly annihilate with electrons of the imaging subject. Each resulting positron-electron annihilation event produces two oppositely directed gamma rays having energies of 511 keV. The gamma rays travel at the speed of light, i.e. about $3 \times 10^8$ meters/see. Since the imaging region 8 typically has a diameter or other characteristic dimension of about two meters or less, the time-of-flight for a gamma particle from the position of the positron-electron annihilation event to one of the radiation detector arrays 10 is a few nanoseconds or less. Thus, the two oppositely directed gam-ma rays strike two of the radiation detectors with typically a sub-nanosecond time differential. The radiation detectors record the radiation detection events, including energy, spatial location, and timestamps, and this data is stored in an events buffer 11.

A gamma ray pair detection circuitry 12 processes the radiation detection events to identify pairs of substantially simultaneous gamma ray detections belonging to corresponding electron-positron annihilation events. This processing can include, for example, energy windowing (that is, discarding radiation detection events outside of a selected energy filtering window disposed about 511 keV) and coincidence-detecting circuitry (that is, discarding radiation detection event pairs temporally separated from each other by greater than a selected time filtering interval). When a gamma ray pair is identified, a line-of-response (LOR) processor 13 processes the spatial information pertaining to the two gamma ray detection events to identify a spatial line of response (LOR) connecting the two gamma ray detections. Since the two gamma rays emitted by a positron-electron annihilation event are oppositely spatially directed, the electron-positron annihilation event is known to have occurred somewhere on the LOR.

In TOF-PET, the radiation detectors 10 have sufficiently high temporal resolution to detect a time-of-flight difference between the two "substantially simultaneous" gamma ray detections. That is, although the radiation detection events occur substantially simultaneously, there is typically a small time difference between the timestamps of the two events due to differences in time-of-flight. This time difference is typically in the sub-nanosecond range. A time-of-flight processor 14 analyzes the time difference between the timestamps of the two substantially simultaneous gamma ray detection events to localize the positron-electron annihilation event along the LOR. The result, accumulated for a large number of positron-electron annihilation events, is a set of histoprojections 15. A reconstruction processor 16 reconstructs the set of histoprojections 15 into a reconstructed image using any suitable reconstruction algorithm, such as filtered backprojection or iterative backprojection with correction. The resulting reconstructed image is stored in an images memory 17, and can be displayed on a user interface 18, printed, stored, communicated over an intranet or the Internet, or otherwise used. In the illustrated embodiment, the user interface 18 also enables a radiologist or other user to control the TOF-PET scanner 8; in other embodiments, a separate controller or control computer may be provided.

Figure 2:
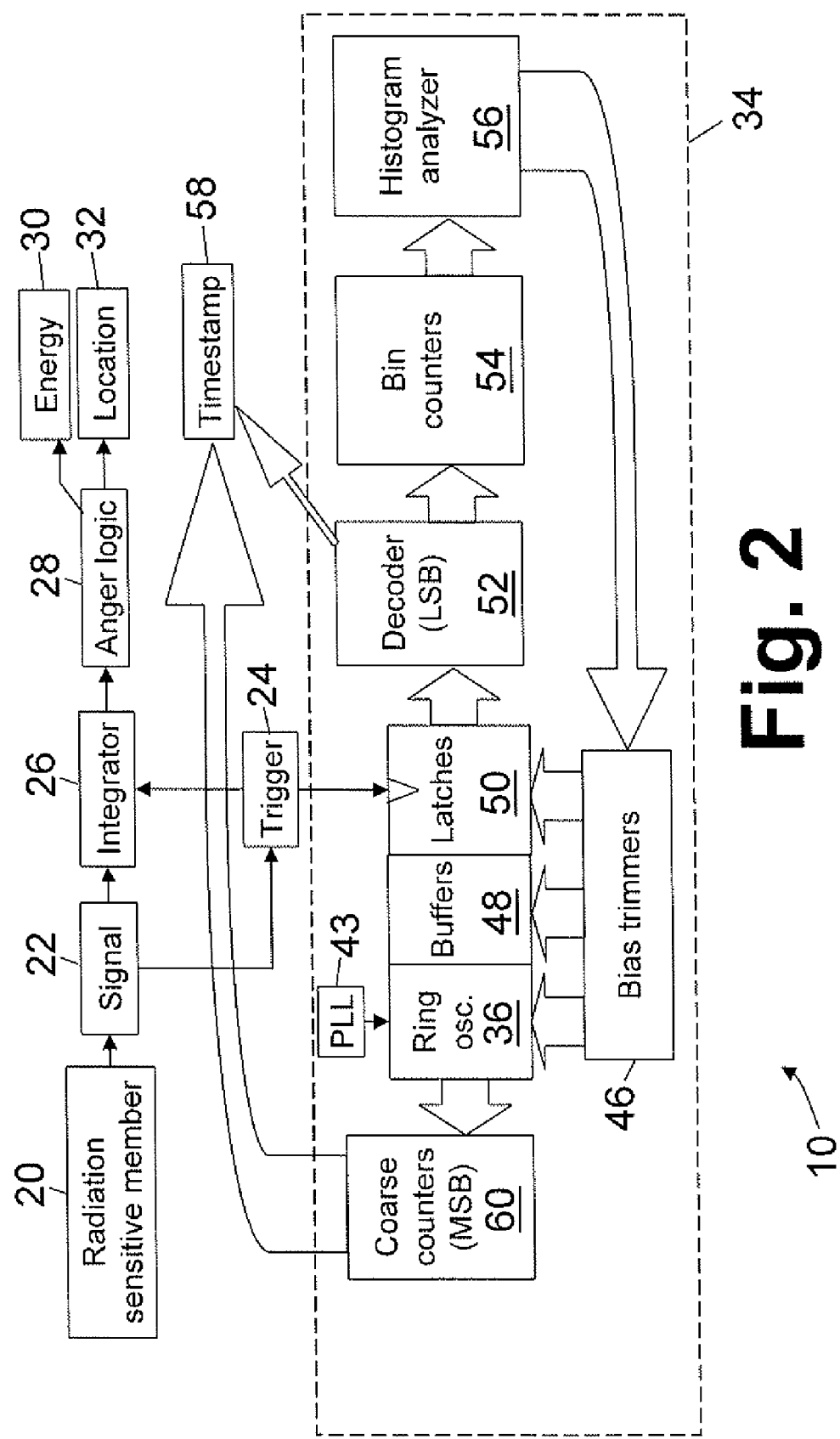

With reference to FIG. 2, the radiation detector array 10 typically includes a radiation-sensitive member 20, which is typically a pixelated array of radiation sensors. In a typical configuration, a scintillation crystal absorbs the 511 keV gamma ray to produce a scintillation of light, and an array of photodetectors, such as photodiodes or photomultiplier tubes (PMTs), detects the scintillation. In other embodiments, a semiconductor-based radiation detector absorbs and detects the gamma ray directly, without an intervening scintillation event. The radiation-sensitive member 20 generates a signal 22 (which may comprise a plurality of signals from a plurality of photodetectors viewing the scintillation event) that is indicative of the radiation detection event. A trigger 24 monitors the signal 22 for a hit, and generates a trigger signal if a hit is detected. The trigger signal is used to initiate integration of the signal by an integrator 26 to produce an integrated signal, which is suitably input to conventional components such as Anger logic 28 process the signal to determine an energy 30 of the incident radiation particle (suitably related to an integral or sum of the scintillation energy seen by one, two, three, or more photodetectors) and a spatial location 32 of the radiation detection event (suitably related to the distribution of scintillation energy seen by the one, two, three, or more photodetectors). The signal 22 also serves as a trigger signal for a time-to-digital converter 34, so as to timestamp the radiation detection event. The time-to-digital converter 34 is based on a ring oscillator 36 having N delay elements.

With reference to FIG. 3, the example ring oscillator 36 having N=16 digital delay elements 40 is illustrated. Although an example N=16 configuration is shown, it is to be appreciated that the number of delay elements can be fewer or more than 16, and the number of delay elements can be other than a power of two (e.g., N=13 is feasible). The digital delay elements 40 are interconnected in series, with the last delay element in the series connecting back with the first delay element to form a ring topology. In general, there are N connections interconnecting N delay elements. Most of the series connections are non-inverting connections; however, one connection 42 in the ring oscillator 36 is an inverting interconnection. In other embodiments, other distributions of inverting and non-inverting interconnections are contemplated. To reduce drift, the ring oscillator 36 is optionally locked to a slower reference clock or oscillator (not shown) via a phase-locked loop (PLL) 43 or other regulation loop.

The PLL 43 in combination with a common reference clock or oscillator can also be used to synchronize multiple ring oscillators, for example to provide time-to-digital conversion for a plurality of radiation detector arrays.

The digital delay elements are biased by high-precision biasing circuitry 44. The use of high-precision biasing circuitry 44 facilitates fixed, non-varying time delays for the digital delay elements 40, whose time delay varies with bias. The example ring oscillator 36 cycles through 32 stable states. To facilitate referencing individual digital delay elements 40 herein, the delay elements in the series are denoted by successive capital letters "A", "B", "C" . . . , "P". The series interconnections feed the output of "A" into "B", the output of "B" (after inversion by the inverting connection 42) into "C", the output of "C" into "D", and so forth, until the output of "P" is fed back into "A" to complete the ring. If the ring oscillator 36 is initialized with all "0" values for the digital delay elements 40, then the initial state of the ring oscillator 36 can be represented as "00-00000000000000", where the symbol "–" denotes the inverting connection. After a delay interval (denoted $T_d$), the ring oscillator 36 transitions to the state "00-10000000000000" with the single "1" value being due to the "0" in the digital delay element "B" being inverted and transferred into the digital delay element "C". The remaining digital delay elements receive non-inverted "0" values, and hence do not change their values. After a second delay interval $T_d$, the ring oscillator 36 transitions to "00-11000000000000", after a third delay interval the ring oscillator 36 transitions to "00-11100000000000", and so forth until after sixteen delay intervals the value "11-11111111111111" is reached. After the seventeenth delay interval $T_d$ the ring oscillator 36 transitions to "11-01111111111111" since now the inverting connection inverts the "1" in delay element "B" into a "0" before it is loaded into delay element "C". After the eighteenth delay interval the ring oscillator 36 transitions to "11-00111111111111", and so forth until after thirty-one delay intervals the ring oscillator 36 transitions to "01-00000000000000", and after the thirty-second delay interval the ring oscillator 36 transitions back to the initial "00-00000000000000" state, thus completing one cycle of the ring oscillator 36 of duration $32 \times T_d$.

The foregoing analysis assumes that all of the digital delay elements 40 have the same delay $T_d$. However, due to mismatch of the digital delay elements 40, this assumption may be substantially in error, even if the bias of all the digital delay elements 40 is the same. That is, if the high-precision biasing circuitry 44 provides exactly the same bias to each and every one of the digital delay elements 40, the delay of these elements may nonetheless differ substantially from one another due to variations between the digital delay elements 40 attributable to manufacturing limits or so forth.

Accordingly, to match the digital delay elements 40 so as to suppress jitter and enhance temporal precision of the ring oscillator 36, each digital delay element 40 additionally has its own individual trimming bias 46. The choice of the biases 44, 46 depends upon the logic style or configuration of the digital delay elements 40, such as for example CMOS or differential current mode logic. In CMOS, the trimming bias 46 may vary a biasing condition of the high precision biasing circuitry 44 such as supply voltage, load capacitance, current limitation, or so forth, so as to independently control the delay of each digital delay element 40. In differential logic, the individual delays are controllable by control of bias current, since the delay is close to inversely proportional to the bias current. Trimming by a mechanism other than bias control is also contemplated.

With continuing reference to FIG. 3 and with further reference back to FIG. 2, a suitable approach for determining values for the individual trim biases 46 is described. The delay elements 40 of the ring oscillator 36 include corresponding readout buffers 48 and latches 50 that receive and hold the digital values of the delay elements 40 responsive to a trigger event. In the case of the radiation detector 10, the trigger event is suitably provided by the trigger signal produced by the trigger 24 indicative of a radiation detection event. A decoder 52 decodes the latched values to produce a state value for the ring oscillator 36. Table 1 provides an example of one possible set of decoder outputs for the 36 different states of the ring oscillator 36. The decoder values of Table 1 are merely examples—the latched values can be mapped to substantially any set of decoder values.

TABLE 1

Example Ring Oscillator State Values

| Latched values | Decoder value (binary) | Decoder value (decimal) | Persistence of the state is related to delay of |
|---|---|---|---|
| 00-00000000000000 | 00000 | 0 | Delay element C |
| 00-10000000000000 | 00001 | 1 | Delay element D |
| 00-11000000000000 | 00010 | 2 | Delay element E |
| 00-11100000000000 | 00011 | 3 | Delay element F |
| 00-11110000000000 | 00100 | 4 | Delay element G |
| 00-11111000000000 | 00101 | 5 | Delay element H |
| 00-11111100000000 | 00110 | 6 | Delay element I |
| 00-11111110000000 | 00111 | 7 | Delay element J |
| 00-11111111000000 | 01000 | 8 | Delay element K |
| 00-11111111100000 | 01001 | 9 | Delay element L |
| 00-11111111110000 | 01010 | 10 | Delay element M |
| 00-11111111111000 | 01011 | 11 | Delay element N |
| 00-11111111111100 | 01100 | 12 | Delay element O |
| 00-11111111111110 | 01101 | 13 | Delay element P |
| 00-11111111111111 | 01110 | 14 | Delay element A |
| 10-11111111111111 | 01111 | 15 | Delay element B |
| 11-11111111111111 | 10000 | 16 | Delay element C |
| 11-01111111111111 | 10001 | 17 | Delay element D |
| 11-00111111111111 | 10010 | 18 | Delay element E |
| 11-00011111111111 | 10011 | 19 | Delay element F |
| 11-00001111111111 | 10100 | 20 | Delay element G |
| 11-00000111111111 | 10101 | 21 | Delay element H |
| 11-00000011111111 | 10110 | 22 | Delay element I |
| 11-00000001111111 | 10111 | 23 | Delay element J |
| 11-00000000111111 | 11000 | 24 | Delay element K |
| 11-00000000011111 | 11001 | 25 | Delay element L |
| 11-00000000001111 | 11010 | 26 | Delay element M |
| 11-00000000000111 | 11011 | 27 | Delay element N |
| 11-00000000000011 | 11100 | 28 | Delay element O |
| 11-00000000000001 | 11101 | 29 | Delay element P |
| 11-00000000000000 | 11110 | 30 | Delay element A |
| 01-00000000000000 | 11111 | 31 | Delay element B |

Also listed in Table 1 is the delay element whose delay controls the persistence of the ring oscillator state. For example, consider the state "00-11000000000000" corresponding to decimal decoder value 2. This state persists until the delay element "E" switches from "0" to "1" due to the presence of the input "1" from delay element "D". Thus, the persistence of state "00-11000000000000" depends upon the delay of the delay element "E". In some embodiments, the persistence of the state "00-11000000000000" (decoder value 2) should be the same as the persistence of the state "11-00111111111111" (decoder value 18) since this state persists until delay element "E" switches from "1" to "0". In other embodiments, the persistence of these two states may be different due to a difference in the delay for the "0"→"1" transition compared with the delay for the "1"→"0" transition.

Figure 4:
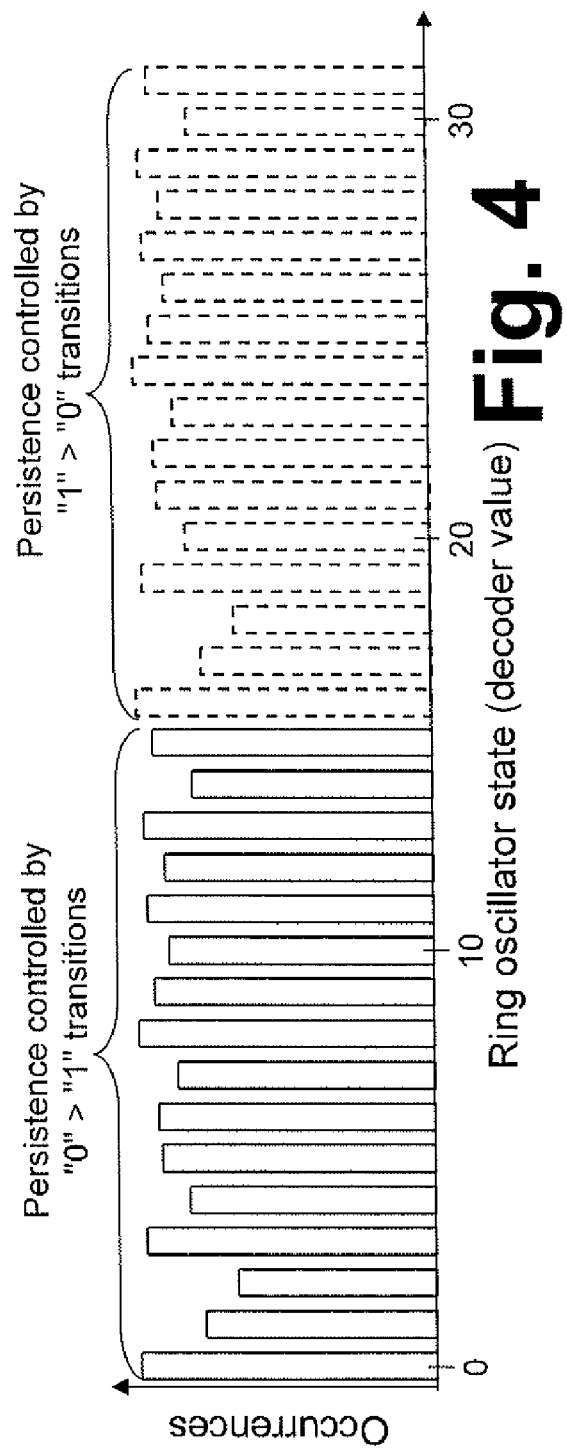
FIG. 4 shows histogram data of the type expected to be acquired by the bin counters of the time-to-digital converter of FIG. 2 before correcting for mismatching of the digital delay elements.
Figure 5:
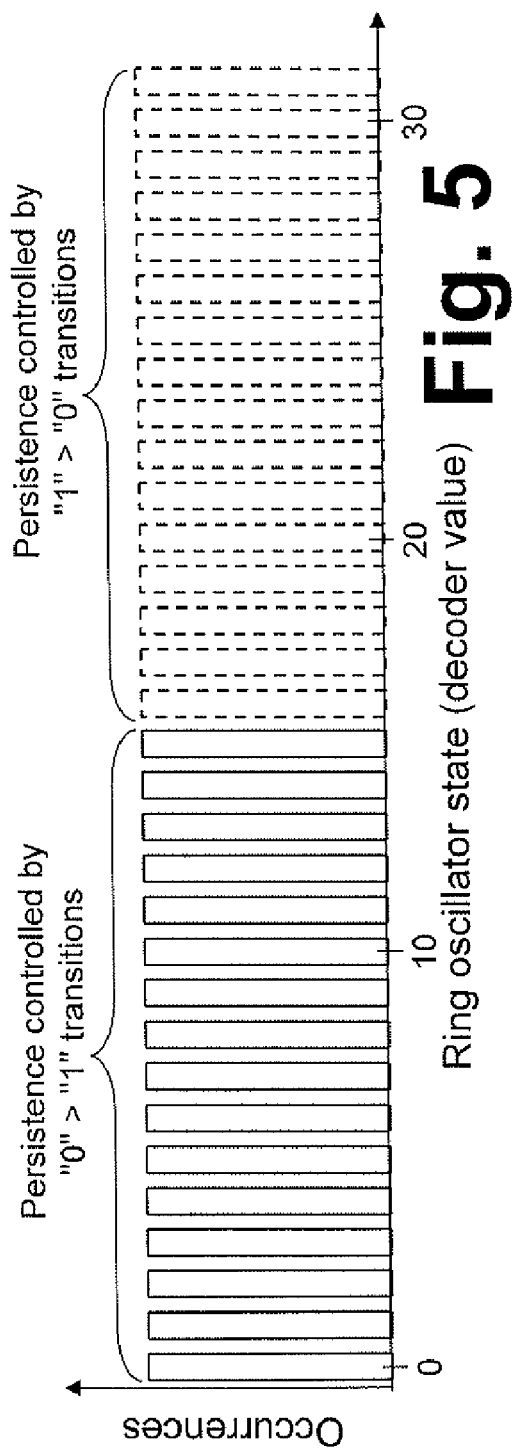
FIG. 5 shows histogram data of the type expected to be acquired by the bin counters of the time-to-digital converter of FIG. 2 after correcting for mismatching of the digital delay elements.

With continuing reference to FIG. 2 and with further reference to FIGS. 4 and 5, the ring oscillator states corresponding to radiation detection events are binned by bin counters 54. The binned ring oscillator state occurrences for the radiation detection events form histogram data. For random radiation detection events but some differences in the delays of the various delay elements 40, the bins of the histogram data are expected to exhibit some variations, such as are plotted in FIG. 4. The radiation detection events should occur randomly in time, since the radioactive decays that generate the positrons occur randomly in time. Accordingly, if the delays for the various digital delay elements 40 are identical, then the histogram of occurrences should be flat to within statistical limits, because the persistence of each ring oscillator state should be the identical. However, if a particular digital delay element has a relatively shorter delay, then the ring oscillator state whose persistence depends upon that delay will occur relatively less frequently. Conversely, if a particular digital delay element has a relatively longer delay, then the ring oscillator state whose persistence depends upon that delay will occur relatively more frequently. The histogram of FIG. 4 is drawn assuming that, for any given digital delay element 40, the "0"→"1" and "1"→"0" transitions have about equal delays. In this case, for example, the persistence of the state "00-11000000000000" (decoder value 2) is the about same as the persistence of the state "11-00111111111111" (decoder value 18) since both are controlled by switching of delay element "E". Hence, the bins for the states "00-11000000000000" and "11-00111111111111" can be combined, and similarly for other inverse-polarity "0"→"1" and "1"→"0" transition pairs, so that the 32 bins of FIG. 4 are reduced to 16 bins. Alternatively, the "0"→"1" and "1"→"0" transitions can be treated separately, in which case 32 bins are employed.

A histogram analyzer 56 analyzes the histogram data, such as the example plot of FIG. 4, to determine the actual delay for each digital delay element 40. For a given individual delay element, the delay is proportional to the number of occurrences of the state or states whose persistence is controlled by the switching of that individual delay element. Accordingly, it is straightforward to determine which delay elements have a relatively longer delay, and which delay elements have a relatively shorter delay. The histogram analyzer 56 adjusts the bias trimmers 46 to lengthen delays that are relatively shorter, and to shorten delays that are relatively longer, so as to obtain a uniform delay that is common for all delay elements 40. For example, in differential logic, the working point is chosen such that the transition speed is close to linear with the bias current, and so a suitable bias current correction is related to a ratio $N_{avg}/N_q$ where $N_q$ is the number of occurrences of a state whose persistence is controlled by the delay element indexed "q" and $N_{avg}$ is the total number of occurrences (i.e., the total number of radiation detection events) divided by the number of bins.

If the "0"→"1" and "1"→"0" transitions are binned separately, then the trim adjustment for a given delay element 40 can be based on the average of the two states whose persistence is controlled by that delay element 40. Alternatively, the digital delay element 40 can be configured such that the delays for the "0"→"1" and "1"→"0" transitions can be independently trimmed, and the trims for the "0"→"1" and "1"→"0" transitions can be adjusted separately.

After trim correction, the bins 54 are optionally cleared and more data acquired. The histogram data acquired after adjustment of the bias trimmers 46 should look similar to that of FIG. 5, in which the histogram of occurrences is flat to within statistical limits indicating a uniform delay $T_d$ that is common for all delay elements 40. Optionally, the correction can be iterative—for example, if the histogram of FIG. 5 continues to show an unacceptable variation in occurrences of various states of the ring oscillator 36, then another bias adjustment can be performed based on the histogram data of FIG. 5. It is contemplated to perform such corrections in substantially real-time, as PET data are acquired. For example, binning can be performed over an interval of a few seconds to a few minutes, followed by adjustment of the bias trimmers 46 based on the collected histogram data, and the cycle repeated iteratively during imaging to provide real-time or close to real-time trimming adjustment.

The range of the bias trimmers 46 should be large enough to correct a worst-case difference in delays of the digital delay elements 40. For example, the "worst-case difference" may be estimated by the expected or experimentally determined manufacturing variations amongst the digital delay elements 40. The adjustment of the trims can be performed during PET imaging, or can be performed in a separate detector calibration run, for example using a phantom having a high concentration of the radioactive substance so as to provide a high number of radioactive detection events so as to speed up the calibration. Instead of using a phantom, radioactive decays, present for example due to natural background radioactivity or contamination of the scintillation material with radioactive elements such as Lu, are a suitable random event generator giving sufficient counts for calibration runs when the imaging device is not in patient data acquisition mode. Moreover, other random triggers can be used to calibrate the time-to-digital converter 34, such as by having a random number generator or analog noise generator to define random trigger events for use in the trim calibration. Indeed, substantially any trigger event that occurs randomly in time at a sufficiently high rate can be used to adjust the bias trimmers 46. The calibration can also be extended to latches and readout buffers, to correct for all differential non-linearity on the analog path of the time-to-digital converter 34.

With reference to FIG. 2, timestamping of radiation detection events during TOF-PET scanning is performed by the trimmed time-to-digital converter 34 as follows. The output of the decoder 52 provides the least significant bits (LSB) for a timestamp 58 computed based at least on the state of the ring oscillator 36 at the time of the trigger event (e.g., signal 22 indicative of a radiation detection event). However, the ring oscillator 36 cycles quickly—typically, a full cycle has a duration of sub-nanoseconds to a few nanoseconds. (For the example ring oscillator 36 having a common delay $T_d$ per delay element 40, the full cycle has duration $32 \times T_d$). To provide timestamps spanning larger timeframes, coarse counters 60 counts cycles, half-cycles, or another temporal unit of the cycling of the ring oscillator 36. For example, in one approach a coarse counter is produced by branching one delay element output to count full cycles of the ring oscillator 36. To avoid transition errors that may occur when the coarse counter increments, a second coarse counter is optionally provided by branching the same but inverted delay element output. The use of two such temporally staggered coarse counters advantageously avoids transition errors. The timestamp 58 is constructed by combining most significant bits (MSB) provided by the coarse counters 60 with least significant bits (LSB) provided by the state of the ring oscillator 36 as indicated by the decoder 52.

With reference to FIG. 6, an approach to improving the temporal resolution of the ring counter-based time-to-digital converter employs oversampling using two sub-delay elements, such as a relatively faster readout buffer 70 and a relatively slower readout buffer 72, per delay element 40. (The delay elements 70, 72 suitably correspond to the readout buffers 48 shown in FIG. 2). The state of each digital delay element 40 is fed in parallel through the fast sub-delay element or readout buffer 70 and the slow sub-delay element or readout buffer 72. The transit time difference of the two readout buffers 70, 72 is roughly adjusted by the transistor geometries and should be ideally half the common bin width (e.g., $T_d/2$). Fine adjustment is suitably provided by having separate biasing circuitry controlling the speed: one biasing circuitry arrangement 74 for the fast readout buffers 70 and another biasing circuitry arrangement 76 for the slow readout buffers 72. Calibration can be performed by using randomly distributed incoming trigger events, resulting in an adjustment targeting an equally distributed hit probability, similar to the trimming circuitry illustrated for the bias trimmers 46 of FIG. 2. By using a pair of the different-speed readout buffers 72, 74 with each digital delay element 40, and feeding outputs of the readout buffers 72, 74 into the latches 50, the effective bin width is reduced (that is, temporal resolution is increased) by a factor of two. In the illustrated example with 16 delay elements 40, each delay element produces two outputs corresponding to the two readout buffers 72, 74, so that 32 latched outputs are provided. Further reduction in bin width can be provided by including three, four, or more different-speed readout buffers per digital delay element 40. For example, with three readout buffers of three different speeds, a factor of three reduction in bin width can be achieved. In some embodiments, each different-speed readout buffer is configured to be individually trimmed.

With reference to FIGS. 7 and 8, another ring oscillator 36' is disclosed, which uses another approach for improving temporal resolution. The ring oscillator 36' includes the digital delay elements 40 interconnected as a ring oscillator. However, the readout buffers 48 are replaced by modified readout buffers 48' with substantially slower "0"→"1" and "1"→"0" transitions, such as the illustrated "0"→"1" transition 80 shown in FIG. 8, which has a slow duration comparable with or exceeding the bin width (denoted $T_{bin}$ in FIG. 8). In contrast, the readout buffers 48 of FIG. 2 have transition times that are substantially shorter than the bin width, so that each digital delay element 40 has a value at the latches 50 that is either "0" or "1" except during the negligibly short transition time. While the illustrated transition 80 is a "0"→"1" transition, the "1"→"0" transition is similarly slow. The output of the readout buffer 48' of each digital delay element 40 serves as input to a sample-and-hold circuit 82 followed by an analog-to-digital converter 84. The output of the readout buffer 48' of each digital delay element 40 is individually digitized by its associated sample-and-hold circuit 82 and analog-to-digital converter 84. In the illustrated embodiment, the analog-to-digital converter 84 is a two-bit converter that provides one of four possible digitized outputs: "00", "01", "10", or "11", as shown in FIG. 8. For example, at the time of the event labeled "Trigger" in FIG. 8, the sample-and-hold circuit 82 takes a snapshot of the delay element signal, which falls within the "01" digitizing level of the analog-to-digital converter 84 such that the analog-to-digital converter 84 outputs "01". An analog-to-digital converter with more bits can be used—for example, a four-bit converter provides sixteen levels ranging from "0000" to "1111". However, fewer bits typically correlates with faster digitization. The digitization allows interpolation of the bin width by sampling the analog value, which interpolation is limited by the resolution of the analog-to-digital converter 84. For the illustrated 2-bit converter, the bin is divided into four sub-bins. More generally, for an M-bit analog-to-digital converter, the bin can be divided into $2^M$ sub-bins.

The outputs of the analog-to-digital converters 84 are input to a decoder 86, which uses combinational logic, reference to a look-up table 88, or so forth to derive the state of the ring oscillator 36' based on the digitized outputs of the analog-to-digital converters 84. In the illustrated embodiment having 16 delay elements 40 and 2-bit analog-to-digital converters 84, the number of states is 128 (16 elements times 2 polarities times 4 digitizing levels), requiring seven bits 90 to represent the output state. Since without the digitizing there would be 32 states (116 elements times 2 polarities, see Table 1) this represents a fourfold decrease in temporal bin width due to the 2-bit analog-to-digital conversion processing. The sample-and-hold circuits 82, analog-to-digital converters 84, and decoding circuitry 86 optionally including the look-up table 88 define a portion of readout circuitry that suitably replaces the readout circuitry portion 50, 52 of the time-to-digital converter 34 of FIG. 2 when the ring oscillator 36' replaces the ring oscillator 36 in the converter 34.

The approach of FIGS. 7 and 8 exploits the full analog information of the ring oscillator. The slow transitions 80, such as the generally "s"-shaped transition 80 of FIG. 8, are automatically translated to a sub-sample axis, which may be linear or substantially linear, by the analog-to-digital conversion. Digital correction can be implemented with the look-up table 88, which can account for transition non-linearities, differences in rise and fall characteristics ("0"→"1" versus "1"→"0" transitions), and so forth. It is also contemplated to account for mismatching between the delay elements 40 or readout buffers 48' by corrections in the look-up table 88. However, in other embodiments the analog-to-digital conversion of FIGS. 7 and 8 is combined with the trimming of FIGS. 2 and 3, with the latter correcting for delay element mismatches. The histogram-based calibration of FIG. 3 can also be used to calibrate the look-up table 88 to provide digitizing sub-bins of uniform bin width. Substantially any type of logic can be used for the ring oscillator 36'. Because the transitions 80 are slow, the delay elements 40 can be designed with substantially reduced bandwidth and lower power. It is contemplated for the transitions 80 to overlap neighboring bins. Such overlap can be advantageous because it facilitates knitting the time axis together across bins on a linear scale.

Various time-to-digital converters have been described with example reference to radiation detector and TOF-PET applications. While described with example reference to radiation detection and TOF-PET applications, the time-to-digital converters disclosed herein will find application in other areas which call for sub-nanosecond timing and timestamping, such as recording radiation detection events for particle physics research, performing high-speed time-sensitive sampling in general, and so forth.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A time-of-flight PET scanner comprising:
   a radiation detector disposed to detect radiation emitted from an imaging region, the radiation detector including at least one time-to-digital converter for timestamping radiation detection events, the time-to-digital converter including:
   a plurality of digital delay elements operatively interconnected as a ring oscillator,
   delay trim elements operatively connected to the digital delay elements and configurable to set a substantially common delay for the digital delay elements, and
   readout circuitry configured to generate a timestamp based at least on a state of the ring oscillator responsive to a radiation detection event.

2. The time-of-flight PET scanner as set forth in claim 1, including a plurality of said radiation detectors disposed to detect radiation emitted from the imaging region, the time-of-flight PET scanner further including:
   pair detection circuitry that identifies two substantially simultaneous radiation detection events based on the timestamps of said radiative detection events;
   a line of response processor that determines a spatial line of response connecting the two radiation detection events; and
   a time of flight processor that localizes a sourcing event along the line of response based on a time difference between the timestamps of the two substantially simultaneous radiation detection events.

3. The time-of-flight PET scanner as set forth in claim 1, wherein the readout circuitry of the time-to-digital converter of the radiation detector further includes:
   coarse counting circuitry for generating a count of a number of state cycles or sub-cycles of the ring oscillator, the readout circuitry generating the timestamp further based on the count.

4. The time-of-flight PET scanner as set forth in claim 1, wherein the time-to-digital converter of the radiation detector further includes:
   circuitry for collecting histogram data of outputs of the ring oscillator responsive to radiation detection events; and
   circuitry for adjusting the delay trim elements based on the histogram data to set the substantially common delay for the digital delay elements.

5. The time-of-flight PET scanner as set forth in claim 1, wherein the delay trim elements of the time-to-digital converter of the radiation detector include:
   biasing circuitry for the digital delay elements, the biasing circuitry being independently controllable to provide independent control of a bias condition of the digital delay elements that affects the delay of the digital delay element.

6. The time-of-flight PET scanner as set forth in claim 1, wherein each digital delay element of the time-to-digital converter of the radiation detector includes:
   two or more sub-delay elements indicative of predetermined portions of the common delay, the readout circuitry computing the state of the ring oscillator with a temporal resolution smaller than the common delay based on the states of the sub-delay elements.

7. A time-to-digital converter comprising:
   a plurality of digital delay elements operatively interconnected as a ring oscillator;
   delay trim elements operatively connected to the digital delay elements and configurable to set a substantially common delay for the digital delay elements; and
   readout circuitry configured to generate an output indicative of a state of the ring oscillator responsive to a trigger event.

8. The time-to-digital converter as set forth in claim 7, wherein the readout circuitry includes:
   coarse counting circuitry for generating a count of a number of state cycles or sub-cycles of the ring oscillator.

9. The time-to-digital converter as set forth in claim 7, further including:
  circuitry for collecting histogram data of outputs of the ring oscillator responsive to randomized trigger events; and
  circuitry for adjusting the delay trim elements based on the histogram data to set the substantially common delay for the digital delay elements.

10. The time-to-digital converter as set forth in claim 7, wherein the digital delay elements have delays dependent upon a bias condition of the digital delay elements, and the delay trim elements include:
  biasing circuitry for the digital delay elements, the biasing circuitry being independently controllable to provide independent control of the bias condition of the digital delay elements.

11. The time-to-digital converter as set forth in claim 7, wherein the digital delay elements have transition times that are substantially shorter than the common delay.

12. The time-to-digital converter as set forth in claim 7, wherein the digital delay elements include readout buffers with transition times that are substantially longer than the common delay, and the readout circuitry includes:
  analog-to-digital converters for digitizing values of the delay elements responsive to the trigger event; and
  decoding circuitry that computes the state of the ring oscillator with a temporal resolution smaller than the common delay based on the digitized values.

13. The time-to-digital converter as set forth in claim 12, wherein the decoding circuitry references a look-up table.

14. The time-to-digital converter as set forth in claim 7, wherein each digital delay element includes:
  two or more sub-delay elements providing oversampling of the common delay.

15. A radiation detector comprising:
  a radiation-sensitive member generating a signal indicative of a radiation detection event; and
  a time-to-digital converter as set forth in claim 7 including readout circuitry configured to generate a timestamp for the radiation detection event based at least on a state of the ring oscillator when the signal is generated.

16. A method for calibrating a ring oscillator comprising a plurality of delay elements operatively interconnected as a ring oscillator, the method comprising:
  determining histogram data of outputs of the ring oscillator responsive to randomized trigger events; and
  adjusting delays of the delay elements based on the histogram data to set a substantially common delay for the delay elements.

17. The method as set forth in claim 16, wherein the adjusting comprises at least one of:
  trimming biasing of a digital element that affects the delay,
  adjusting analog-to-digital conversion parameters used in sub-bin width resolution readout of the ring oscillator, and
  adjusting delays of oversampling readout buffers used in sub-bin width resolution readout of the ring oscillator.

18. A time-to-digital converter comprising:
  a plurality of digital delay elements operatively interconnected as a ring oscillator, the digital delay elements including readout buffers having transition times that are substantially longer than a delay of the digital delay elements;
  analog-to-digital converters for digitizing values of the delay elements responsive to a trigger event; and
  decoding circuitry that computes a state of the ring oscillator corresponding to the trigger event based on the digitized values, the computed state having a temporal resolution smaller than the delay of the digital delay elements.

19. The time-to-digital converter as set forth in claim 18, wherein the analog-to-digital converters include:
  sample-and-hold circuits that acquire analog values of the digital delay elements; and
  analog-to-digital conversion circuits coupled with the sample-and-hold circuits to digitize the analog values with at least a two-bit resolution.

20. The time-to-digital converter as set forth in claim 18, wherein the decoding circuitry of the time-to-digital converters of the radiation detectors references a look-up table.

21. A radiation detector comprising:
  a radiation-sensitive member generating a signal indicative of a radiation detection event; and
  a time-to-digital converter as set forth in claim 18, in which the analog-to-digital converters are configured to digitize values of the delay elements responsive to the signal indicative of a radiation detection event.

22. A time-of-flight PET scanner comprising:
  radiation detectors each including a radiation-sensitive member configured to generate a signal indicative of a radiation detection event and a time-to-digital converter as set forth in claim 18 configured to construct a timestamp for the radiation detection event based at least on the state of the ring oscillator;
  pair detection circuitry that identifies two substantially simultaneous radiation detection events based on the digitized values of said radiative detection events;
  a line of response processor that determines a spatial line of response connecting the two radiation detection events; and
  a time of flight processor that localizes a sourcing event along the line of response based on a time difference between the timestamps of the two substantially simultaneous radiation detection events.

* * * * *